United States Patent [19]

Kaerwer

[11] Plant 4,465

[45] Oct. 23, 1979

[54] KENTUCKY BLUEGRASS PLANT

[75] Inventor: Howard E. Kaerwer, 12800 Gerard Dr., Eden Prairie, Minn. 55344

[73] Assignee: Howard E. Kaerwer, Eden Prairie, Minn.

[21] Appl. No.: 918,164

[22] Filed: Jun. 22, 1978

[51] Int. Cl.[2] ..... A01H 5/00

[52] U.S. Cl. ..... Plt./88

[58] Field of Search ..... Plt./88

[56] References Cited

U.S. PATENT DOCUMENTS

P.P. 3,176 5/1972 Daniel ..... Plt./88

*Primary Examiner*—Robert E. Bagwill

*Assistant Examiner*—James R. Feyrer

*Attorney, Agent, or Firm*—Phillip H. Smith

[57] ABSTRACT

A Kentucky bluegrass plant which exhibits high turf quality, even when grown under low to moderate nitrogen fertility levels and restricted moisture. The plant has a medium dark green color, a medium leaf texture, high tiller density, rapid greening in the spring, good fall color retention, excellent low mowing tolerance, a vigorous and spreading growth habit, rapid seed germination and vigorous establishment, sustained turf quality through entire season, high resistance to common turf grass diseases, and a sustained high seed yield when managed for seed production.

3 Drawing Figures

ORIGIN OF THE CULTIVAR

The present cultivar of Kentucky bluegrass plant was discovered in a collecton of bluegrass plants collected from an old turf area in the city park in Peoria, Ill. Kentucky bluegrass plants from this collection were vegatively or asexually propagated in a greenhouse of Northrup King Co., Minneapolis, Minn., and transplanted to a growing field of Northrup King Co. for further observation and selection. The present cultivar was identified as U.S. Plant Pat. No. 4,183 of the collection, and the cultivar exhibited distinct and superior characteristics over the remainder of the population.

Seed of U.S. Plant Pat. No. 4,183 was produced and placed into numerous turf evaluation trials for experimental testing as cultivar K1-155 Kentucky Bluegrass. Upon receipt of favorable test reports from the north central, eastern, southern, and western United States, as well as Canada and Europe, it was concluded that K1-155 represented a new and distinct superior performing cultivar of Kentucky bluegrass plant. The cultivar was subsequently named Rugby. Foundation seedstock planting have been established for commercial introduction of the cultivar under the name Rugby.

ASEXUAL REPRODUCTION OF THE CULTIVAR

The present cultivar of Kentucky bluegrass has been asexually reproduced at the facilities of Northrup King Co. of Minneapolis, Minn. U.S. Plant Pat. No. 4,183 is reproduced true to type when propagated asexually. Asexual reproduction of the variety by propagules (tillers and rhizomes) and by disseminules (modified caropses producted by agamospermy) has consistently produced progeny plants indistinguishable from the mother plant.

The original parent close of U.S. Plant Pat. No. 4,183 is maintained as seedstock by Northrup King Co., Minneapolis, Minn.

The present cultivar is highly apomictic. Examinations of the progeny produced from U.S. Plant Pat. No. 4,183 indicate approximately 85% to 90% apomictic reproduction. The majority of the aberrant plants display weak vigor, and they often die or become crowded out by the more aggressive and vigorous typical plants. The genetic aberrants are generally similar to U.S. Plant Pat. No. 4,183 in plant height and maturity, but vary primarily for color, leaf texture, vigor, and certain morphological features. The cultivar can be easily rogued to remove these aberrants when grown in typical seed production row plantings.

SUMMARY OF THE CULTIVAR

The present cultivar identified herein by its original U.S. Plant Pat. No. 4,183 or its subsequent turf trial No. K1-155 or its cultivar name Rugby, exhibits a unique combination of characteristics which distinguish it from all other cultivars of which I am aware. Of particular importance is the ability of the cultivar to provide a high level of turf quality when not intensively cultured (as when grown under low to moderate nitrogen fertility levels, non-regular mowing, and restricted moisture levels), as well as providing high turf quality when intensively cultured (as with moderate to high nitrogen levels, ample irrigation, and frequent mowing). The present exhibits the following more detailed characteristics:

1. A medium dark green, attractive turf color, even when grown under low to moderate nitrogen fertility levels and restricted moisture;
2. A medium leaf texture;
3. A high tiller density;
4. A rapid rate of greening in the spring;
5. Very good color retention in late fall;
6. Excellent tolerance of mowing as close as 0.5 inch;
7. An aggressive vigorous, spreading growth habit;
8. Rapid seed germination and vigorous establishment;
9. Sustained turf quality from early spring, through summer, and late into fall;
10. A sustained high seed yield when managed for seed production.

In addition, Rugby possesses a high level of resistance to most of the common turfgrass diseases:

1. Excellent resistance to leafspot and melting out incited by *Helminthosporium vagans* (*Drechslera poae*);

2. Excellent resistance to powdery mildew incited by *Erysiphe graminis;*

3. Excellent resistance to date to Fusarium blight incited by *Fusarium roseum* and *F. tricinctum* in trials where less resistant cultivars have been seriously damaged by the disease;

4. Excellent resistance to dollar spot incited by *Sclerotinia homeocarpa;*

5. Good resistance to stem rust incited by *Puccinia graminis;*

6. Moderate resistance to stripe rust incited by *Puccinia striiformis.*

BRIEF DESCRIPTION OF THE DRAWING

The drawing includes

DESCRIPTION OF THE CULTIVAR

Figure 1:
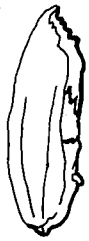
FIG. 1, which is a lateral view of a typical seed of the cultivar.

The present cultivar is a tufted, rhizomatous, perennial Kentucky bluegrass plant (*Poa pratensis*) which possesses the following combination of morphological characteristics which distinguishes it from other Kentucky bluegrass cultivars, the cultivar being identified by its original U.S. Plant Pat. No. 4,183.

Culms

The culms of U.S. Plant Pat. No. 4,183 are erect but usually bent at the lower nodes. The culms are tufted, moderately stout (1.0 to 1.5 m diameter), compressed-cylindrical in cross section, smooth and glossy, and usually 3 to 5 noded. When unmown, the culms average 68 cm in length.

Leaves

The leaves of U.S. Plant Pat. No. 4,183 are initially folded but subsequently open out to a flat leaf with a hooded, boat shaped tip. The leaf shoot is compressed and keeled on the back. The leaves are dark green. The collar margin is fringed with fine hairs and there is moderate hairiness at the top of the sheath near the junction of the leaf blade. There is no hair on the margin of the sheath and very little hairiness on the sides and back of the sheath. The leaf blade is hairless. The ligule of vegetative leaves is membraneous, short, hairy, and truncate in shape. Leaf blade width averages 4.1 mm wide from two-year old space planted clones mown at 3 inches. Leaf length of unmown clones averages 66 cm long. The base of the sheath in young seedlings is green with little tendency toward red pigmentation.

When maintained as space planted clones, the average spread of two-year old plants grown in Minnesota is 80 cm diameter.

Flag Leaves

Flag leaves of U.S. Plant Pat. No. 4,183 are appressed. Flag leaf length ranges from 25 to 66 mm (average 42 mm) and the flat leaf width ranges from 4.0 to 7.0 mm wide (average 4.4 mm). The flag leaf sheath ranges from 70 to 110 mm long (average 91 mm). The collar margin is lightly hairy to hairless, the sheath and sheath margins are hairless, and the ligule is slightly hairy. The ligule length of reproductive tillers averages 1.7 mm long.

Panicles

The panicles of U.S. Plant Pat. No. 4,183 are pyramidal, loosely open, with the central rachis mostly erect. The length of the rachis ranges from 63 to 99 mm (average 77 mm). The panicle emerges from the sheath green and the branches are tightly appressed, gradually lowering until the lowest branches are horizontal at anthesis. After flowering, the branches become somewhat more erect and the panicle ripens to a golden tan. The seedheads sometimes develop a slight reddish or bronze cast, due to red or bronze pigmentation of the margins of the lemmas. The collar of the lowest panicle node is distinctly closed and the rachis at the node is straight, not humped or bent.

Plant maturity is about equal to the cultivars Merion and Parade; later than the cultivars Park and Newport and slightly earlier than the cultivar Glade.

Spikelets

The spikelets of U.S. Plant Pat. No. 4,183 are ovate, compressed, 3.2 to 6.0 mm long (average 4.3 mm), 3 to 5 flowered (average 3.8 florets per spikelet), breaking up at maturity beneath each lemma. The glumes are persistent, pointed, unequal in length, and rough on the keels. Lower glume 1 to 3 nerved, average 2.7 mm long. Upper glume 3 nerved, average 3.0 mm long. Lemmas are overlapping, 5 nerved, flared at the apex, rounded on the back, intermediate nerves obscure or lacking. The lemma has hair on the keel and margins from the callus midway up the lemma. There is long, fine, crinked hair at the base of the lemma. Margins of the lemmas often tinged with red or bronze, giving the seedhead a slight reddish or bronze cast. The paleas are about as long as the lemmas and tightly enclosed by the lemma. Hairs on the keels of the palea are coarse. The caryopsis is tightly encased by the lemma and palea; it is short and thick at the middle, often causing a transverse wrinkle on the palea. Floret size is approximately 2.5 to 3.0 mm long and 0.75 to 1.0 mm wide.

Morphological examinations of the present cultivar, U.S. Plant Pat. No. 4,183, indicated by the cultivar name Rugby, are presented in Tables 1 and 2.

Environmental factors may influence morphological characteristics to some extent, and accordingly the location of the tests and trials conducted is indicated in the following tables.

Turf Performance of the Cultivar

The present cultivar, U.S. Plant Pat. No. 4,183, identified in the following tables by the varietal name Rugby, provides a high quality turf over a broad range of cultural conditions throughout most of the bluegrass growing area of the United States, Canada, and Europe. The following tables illustrate this characteristic:

Tables 3 and 4 present turf quality, density, and color ratings from the trials of Northrup King Co., at Eden Prairie, Minn. These trials receive 2.5 to 5.0 pounds of nitrogen per thousand square feet per growing season; they are irrigated as needed; then are mown at 0.6 inch and 2.0 inches twice per week and the clippings are removed. Under these conditions, Rugby produces a high quality turf and sustains a high level of quality from one growing season to the next.

These data indicates that Rugby maintains a satisfactory shoot density even at a low mowing height. In addition, these data illustrates that for Rugby, the color is satisfactory during midsummer and very good in spring and late fall. The late fall attractiveness of Rugby is especially notable and is illustrated in Table 3.

Tables 5 and 6 present turf quality, density, color, and dormancy ratings for Rugby and other bluegrass cultivars when grown under suboptimal cultural conditions at Eden Prairie, Minn. These trials are maintained with no annual nitrogen fertilization and they receive no irrigation other than natural rainfall. These trials are mown as needed to 2 inches, and the clippings are picked up. It may be seen from this data that Rugby provides a high level of turf quality when grown at a low cultural intensity. It maintains a dense stand when most other cultivars begin to thin out. In addition, Rugby maintains a darker green color under these conditions than most other bluegrass cultivars. Under low fertility and restricted moisture, Rugby displays rapid spring greenup, little tendency toward dormancy, rapid recovery from midsummer dormancy, and it sustains its green color late into the fall.

Table 7 presents turf quality and color comparisons for Rugby and other bluegrass cultivars grown at Woodland, Calif., under high management cultural conditions. This data indicates Rugby provides a satisfactory level of turf quality sustained from one growing season to the next in the prevailing climatic conditions of northern California.

Seasonal Growth Cycle of the Cultivar

The present cultivar, identified by the varietal name Rugby, exhibits a unique seasonal growth pattern compared to other bluegrass cultivars. Tables 3, 8, and 10 illustrate for Rugby the rapid spring greenup rate when intensively managed at high nitrogen fertility levels and with adequate irrigation. Tables 5, 6, and 9 illustrate for Rugby the superior early spring and late fall color even when maintained with low nitrogen fertility and restricted moisture. It should be noted that under both levels of management, Rugby typically displays early spring initiation of growth, sustained growth even during the midsummer heat stress period, and excellent growth vigor late into the fall.

The present cultivar, Rugby, has the ability to produce many short seedheads in a mown turf during the late spring and early summer months. These seedheads may detract from the quality of the turf for a short time in early summer, but they are usually mown out of the turf by midsummer. Tables 11 and 12 compare this seedhead formation tendency in Rugby and other bluegrass cultivars.

Disease Resistance of the Variety

Leafspot (Helminthosporium ssp.)

The high level of resistance to Helminthosporium leafspot and melting out for the present variety, Rugby, is presented in Tables 13, 14, and 15. It is apparent from these data that Rugby possesses a level of resistance equal to or superior to most other bluegrass cultivars when grown at both low and high nitrogen fertility levels.

Fusarium Blight (*F. roseum/F. tricinctum*)

The tolerance to Fusarium blight of Rugby is presented in Tables 16, 17, 18, 19, and 20. From these data, it may be seen that Rugby is sustaining a high level of resistance in trial situations where the disease incidence is severe and less resistant cultivars have been seriously damaged. Table 16 illustrates that Rugby has maintained its Fusarium blight resistance both at a moderate nitrogen rate as well as at a high nitrogen rate. Table 17 indicates that Rugby sustains its Fusarium blight resistance from season to season, whereas damage in other cultivars may vary from season to season. Table 19 illustrates Rugby can withstand an induced chemical herbicide stress with subsequent Fusarium blight development better than most other cultivars.

Dollar Spot (*Sclerotinia homeocarpa*)

The resistance of Rugby to dollar spot disease is presented in Tables 21 and 22. From these data, it is apparent that Rugby displays equivalent or superior resistance to dollar spot compared to other bluegrass cultivars.

Rusts (Puccinia ssp.)

Rugby is moderately resistant to both stem rust and stripe rust. Tables 23, 24, and 25 illustrate the resistance of Rugby to stem rust when managed as a turf. Table 26 indicates a satisfactory level of stripe rust resistance in California.

Powdery Mildew (*Erysiphe graminis*)

Rugby displays an acceptable level of resistance to powdery mildew. Table 27 illustrates this resistance in a trial situation where mildew incidence was extensive in many cultivars.

Stripe Smut (*Ustilago striiformis*)

Rugby is moderately susceptible to stripe smut damage. Tables 28 and 29 compare the incidence of this disease in Rugby and other bluegrass cultivars in two locations.

Seed Characteristics of the Variety

Figure 2:
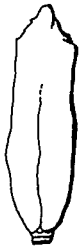
FIG. 2, which is a dorsal view of a typical seed of the cultivar.
Figure 3:
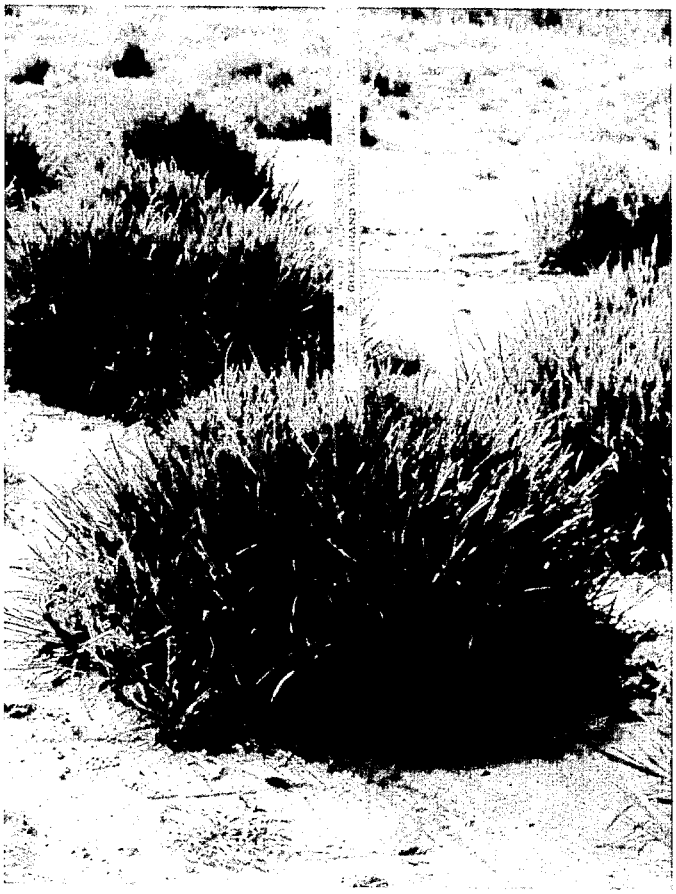
FIG. 3 comprises a photograph of a typical clone of the plant, which plant was approximately one year old when the photograph was taken, and showing the early heading stage of the plant.

Referring to FIGS. 1 and 2 of the drawings, FIG. 1 shows a lateral view of a typical seed, and FIG. 2 shows a dorsal view thereof, both figures being produced at a scale wherein ½ inch in the drawings equals 1 millimeter for the seed. The seed length is 2½–3 mm, and the width is ¾–1 mm.

Typical seeds of the present cultivar are shorter and more broadly oblong in comparison to seed for other cultivars of Kentucky bluegrass.

The lemma is rounded on the back. Intermediate nerves are obscure or lacking, and the apex is flared. The hairs on the keels of the palea are coarse. The caryopsis is short and thick at the middle, often causing a transverse wrinkle on the palea.

Seed Production Characteristics of the Cultivar

Rugby is a high seed yielding cultivar which provides a moderately high seed yield in a first year seed production field and which provides sustained, high seed yields in subsequent crop years.

TABLE 1

Morphological comparison of Rugby and other bluegrass cultivars grown in a greenhouse at Eden Prairie, Minnesota(1) for 12 weeks.

| | Leaf width mm | Hair on collar margin | Hair on sheath margin | Hairtuft on sheath at top of the sheath |
|---|---|---|---|---|
| Rugby | 2.4 | 5.2(2) | 1.0(2) | 2.9(2) |
| Vantage | 3.0 | 5.2 | 2.6 | 2.8 |
| Baron | 2.7 | 3.7 | 1.3 | 4.3 |
| Majestic | 2.0 | 3.6 | 1.6 | 2.8 |
| Victa | 2.8 | 3.7 | 1.4 | 3.9 |
| Toughdown | 2.6 | 2.7 | 1.0 | 1.5 |
| Park | 2.1 | 1.8 | 1.0 | 1.3 |
| Pennstar | 2.0 | 2.7 | 1.0 | 1.7 |
| Bristol | 2.3 | 3.7 | 1.2 | 2.2 |
| Bonnieblue | 2.3 | 3.0 | 1.3 | 2.2 |
| Glade | 2.3 | 3.6 | 1.1 | 2.1 |
| Nugget | 2.2 | 7.1 | 2.8 | 3.8 |
| Fylking | 2.1 | 2.9 | 1.8 | 1.7 |
| Newport | 2.5 | 4.4 | 2.6 | 3.5 |

TABLE 1-continued

Morphological comparison of Rugby and other bluegrass cultivars grown in a greenhouse at Eden Prairie, Minnesota(1) for 12 weeks.

| | Hair on sheath sides and back | Hair on upper leaf surface | Hair on ligule |
|---|---|---|---|
| Rugby | 1.7(2) | 1.0(2) | 3.5(2) |
| Vantage | 1.6 | 1.6 | 2.8 |
| Baron | 2.7 | 1.0 | 4.6 |
| Majestic | 2.0 | 1.2 | 2.7 |
| Victa | 2.5 | 1.0 | 4.1 |
| Touchdown | 1.0 | 1.0 | 1.7 |
| Park | 1.1 | 3.6 | 1.1 |
| Pennstar | 1.2 | 1.0 | 1.2 |
| Bristol | 1.0 | 1.0 | 1.6 |
| Bonnieblue | 1.0 | 1.0 | 1.4 |
| Glade | 1.0 | 1.0 | 1.7 |
| Nugget | 2.3 | 1.0 | 2.3 |
| Fylking | 1.0 | 1.0 | 1.4 |
| Newport | 1.1 | 1.0 | 5.2 |

(1)Grown at Northrup King Co. greenhouse. Test seeded fall 1977. Grown under natural photoperiod supplemented with fluorescent light to give 24-hour photoperiod for 8 weeks, then maintained with natural photoperiod from an additional 4 weeks.
(2)1 to 9; 1 = no hairs, 9 = many hairs.

TABLE 2

Agronomic comparison of Rugby and other bluegrass cultivars grown at Eden Prairie, Minnesota(1).

| | Growth habit(2) 6/24/75 | Plant height(cm) 6/24/75 | Relative maturity(3) 5/13/76 |
|---|---|---|---|
| Rugby | 7.6 | 68 | 7.4 |
| Delta | 9.0 | 74 | 2.0 |
| Nugget | 6.0 | 35 | 5.0 |
| Merion | 5.9 | 49 | 7.3 |
| Baron | 7.2 | 50 | 7.7 |
| Newport | 7.8 | 61 | 6.0 |
| Pennstar | 6.1 | 49 | 7.0 |
| Parade | 7.0 | 68 | 7.8 |
| Sydsport | 6.4 | 54 | 7.2 |
| Park | 6.8 | 77 | 6.3 |
| Fylking | 5.0 | 46 | 6.3 |
| Glade | 5.0 | 45 | 8.6 |

| | Relative number of panicles per plant(4) | | |
|---|---|---|---|
| | 6/24/75 | 5/28/76 | 2-year average |
| Rugby | 3.0 | 2.5 | 2.8 |
| Delta | 3.0 | 1.0 | 2.0 |
| Nugget | 5.0 | 2.0 | 3.5 |
| Merion | 5.0 | 4.0 | 4.5 |
| Baron | 5.0 | 3.0 | 4.0 |
| Newport | 5.0 | 1.0 | 3.0 |
| Pennstar | 5.5 | 5.0 | 5.3 |
| Parade | 3.0 | 3.0 | 3.0 |
| Sydsport | 3.0 | 2.0 | 2.5 |
| Park | 5.0 | 2.0 | 3.5 |
| Fylking | 6.3 | 6.0 | 6.2 |
| Glade | 6.0 | 3.0 | 4.5 |

(1)Grown at Northrup King Co. greenhouse. Test seeded in 1974
(2)1 to 9; 1 = prostrate, 9 = erect.
(3)1 to 9; 1 = early, 9 = late
(4)1 to 9; 1 = many, 9 = none

TABLE 3

Relative Turf Quality, Density, Color, and Fall Appearance Ratings of Rugby and Other Bluegrass Cultivars at Eden Prairie, Minnesota(1)

| | Turf Quality Average of 2.0 and 0.6 inch mowing heights | | | | Density 2 inch |
|---|---|---|---|---|---|
| | 1974 | 1975 | 1976 | 3-Year Mean | 1975–76 Avg. |
| Rugby | 4.2(2) | 4.5 | 4.9 | 4.5 | 4.0(2) |

TABLE 3-continued

Relative Turf Quality, Density, Color, and Fall Appearance Ratings of Rugby and Other Bluegrass Cultivars at Eden Prairie, Minnesota(1)

| | | | | | |
|---|---|---|---|---|---|
| Pennstar | 4.2 | 4.1 | 3.9 | 4.1 | 4.2 |
| Fylking | 4.3 | 3.9 | 3.6 | 3.9 | 4.0 |
| Merion | 5.1 | 5.4 | 4.7 | 5.1 | 4.8 |
| Adelphi | 4.6 | 4.9 | 4.7 | 4.7 | 4.8 |
| Glade | 3.5 | 4.4 | 4.7 | 4.2 | 3.8 |
| Baron | 4.0 | 5.2 | 4.6 | 4.6 | 4.3 |
| Victa | 4.3 | 5.1 | 4.8 | 4.7 | 4.8 |
| Vantage | 6.2 | 5.7 | 5.1 | 5.7 | 5.8 |
| Parade | 4.5 | 4.9 | 4.6 | 4.7 | 4.6 |
| Nugget | 5.0 | 4.1 | 4.3 | 4.5 | 3.8 |
| Newport | 4.8 | 5.5 | 5.9 | 5.4 | 5.4 |
| Park | 5.3 | 6.0 | 6.0 | 5.8 | 6.2 |
| South Dakota Cert. | 5.7 | 6.3 | 5.7 | 5.9 | 6.3 |

| | Color 2 Inch | | | Late fall Attractiveness 2 Inch |
|---|---|---|---|---|
| | Aug. 1975 | Fall 1975 | Spring 1976 | 1975–76 Avg. |
| Rugby | 5.0(2) | 3.5 | 3.5 | 3.8(2) |
| Pennstar | 4.8 | 3.6 | 3.7 | 3.7 |
| Fylking | 5.3 | 3.9 | 3.8 | 3.4 |
| Merion | 5.1 | 4.1 | 4.0 | 5.4 |
| Adelphi | 4.7 | 3.2 | 3.1 | 4.4 |
| Glade | 4.0 | 3.3 | 3.5 | 3.5 |
| Baron | 4.5 | 3.5 | 3.5 | 4.5 |
| Victa | 5.0 | 3.0 | 3.8 | 4.6 |
| Vantage | 5.0 | 3.8 | 4.8 | 5.3 |
| Parade | 5.3 | 3.8 | 3.6 | 3.9 |
| Nugget | 3.0 | 3.0 | 2.8 | 4.3 |
| Newport | 4.7 | 4.0 | 4.8 | 4.9 |
| Park | 5.0 | 4.5 | 5.4 | 5.6 |
| South Dakota Cert. | 4.5 | 3.8 | 4.8 | 5.1 |

(1)Northurp King Co. Test seeded fall, 1973. Irrigated as needed; 4 to 5 lbs. N/M/season.
(2)1 to 9; 1-highest quality, darkest green, or most density.

TABLE 4

Relative turf quality, color, and density ratings for Rugby and other bluegrass cultivars at Eden Prairie, Minnesota(1).

| | Turf Quality 2 Inch Cut | Color 2 Inch Cut | Density 1977 | | |
|---|---|---|---|---|---|
| | 1976–77 Mean | 1977 | 0.5 Inch | 2 Inch | Mean |
| Rugby | 4.0(2) | 4.3(2) | 5.2(2) | 5.5 | 5.5 |
| Adelphi | 4.1 | 3.6 | 4.1 | 4.7 | 4.4 |
| Pennstar | 4.8 | 4.3 | 5.5 | 5.5 | 5.5 |
| Fylking | 4.7 | 4.3 | 5.5 | 5.5 | 5.5 |
| Park | 5.7 | 5.3 | 5.7 | 5.3 | 5.5 |
| Merion | 5.1 | 4.3 | 5.3 | 4.7 | 5.0 |
| Nugget | 5.5 | 3.3 | 5.5 | 4.5 | 5.0 |
| Parade | 3.8 | 4.3 | 3.5 | 5.5 | 4.5 |
| Baron | 5.5 | 4.3 | 5.5 | 4.5 | 5.0 |
| Glade | 4.6 | 3.8 | 4.5 | 4.0 | 4.3 |
| Bonnie-blue | 4.3 | 5.0 | 4.5 | 4.5 | 4.5 |
| Victa | 4.2 | 4.8 | 4.5 | 3.5 | 4.0 |
| Vantage | 3.8 | 4.5 | 4.0 | 5.0 | 4.5 |
| A-34 | 4.9 | 5.3 | 4.0 | 4.5 | 4.3 |
| Touch-down | 4.7 | 3.8 | 4.5 | 3.5 | 4.0 |

(1)Northrup King Co. Test seeded fall 1975. Irrigated as needed; 2 to 3.5 lbs. N/M/season.
(2)1 to 9; 1-best quality, darkest green, or most density.

TABLE 5

Relative turf quality, density, color, and spring greenup ratings of Rugby and other bluegrass cultivars when grown under low nitrogen fertility levels and not irrigated, at Eden Prairie, Minnesota(1).

| | Turf quality 2 Inch cut 1974–76 Avg. | Density 2 Inch cut 1974–76 Avg. | Color 2 Inch cut 1974–76 Avg. | Spring greenup 2 Inch cut 1975–76 Avg. |
|---|---|---|---|---|
| Rugby | 4.0(2) | 3.9(2) | 4.0(2) | 5.3(2) |
| Nugget | 6.0 | 6.7 | 3.9 | 8.0 |
| Park | 5.6 | 4.7 | 5.6 | 5.2 |
| Parade | 4.4 | 4.2 | 4.4 | 5.1 |
| Adelphi | 4.6 | 5.1 | 4.3 | 6.0 |

(1)Northrup King Co. Test seeded spring 1973. Test is non-irrigated and receives no annual nitrogen fertilization.
(2)1 to 9; 1 = highest quality, darkest green, most density, or rapid greenup.

TABLE 6

Relative Turf Quality, Density, Fall Color, and Fall Greenup Ratings for Rugby and Other Bluegrass Cultivars when Grown Under a Low Nigrogen Fertility Level and Not Irrigated, at Eden Prairie, Minnesota(1)

| | Turf Quality 2 Inch Cut 1975–76 Avg. | Density 2 Inch Cut 1975–76 Avg. | Fall Color 2 Inch Cut October, 1975 | Fall Greenup (Recovery) from Summer Dormancy 2 Inch Cut 1975–76 Avg. |
|---|---|---|---|---|
| Rugby | 3.8[2] | 6.0[2] | 4.0[2] | 4.3[2] |
| Park | 5.1 | 5.4 | 4.7 | 5.9 |
| Parade | 4.5 | 5.8 | 3.5 | 3.5 |
| Adelphi | 5.3 | 6.8 | 4.5 | 4.5 |
| Enmundi | 5.8 | 6.3 | 5.0 | 5.2 |
| Baron | 5.8 | 6.5 | 4.5 | 6.2 |

(1)Northrup King Co. Test seeded fall 1974. Test is non-irrigated and receives no annual nitrogen fertilization.
(2)1 to 9; 1 = highest quality, most density, darkest green, or rapid greenup.

TABLE 7

Relative Turf Quality and Color Ratings for Rugby and Other Bluegrass Cultivars at Woodland, California(1)

| | Turf Quality | | | | |
|---|---|---|---|---|---|
| | 1974 | 1975 | 1976 | 3 Year Mean | Color April 1976 |
| Rugby | 4.7[2] | 5.1 | 6.1 | 5.3 | 4.0[2] |
| Glade | 4.5 | 4.7 | 6.1 | 5.1 | 3.5 |
| Adelphi | 4.4 | 4.1 | 5.6 | 4.7 | 3.0 |
| Parade | 4.0 | 3.6 | 5.2 | 4.3 | 4.5 |
| Baron | 4.2 | 4.6 | 5.3 | 4.7 | 3.0 |
| Fylking | 5.0 | 4.4 | 6.0 | 5.2 | 4.0 |
| Sydsport | 4.5 | 5.0 | 5.8 | 5.1 | 3.0 |
| Park | 5.2 | 3.8 | 5.6 | 4.9 | 5.0 |
| Pennstar | 5.0 | 5.1 | 5.7 | 5.3 | 4.4 |
| Merion | 4.7 | 4.8 | 5.7 | 5.1 | 4.4 |

(1)Northrup King Co. Test seeded spring of 1973. Data is the average from 0.8 inch and 2.0 inch mowing heights.
(2)1 to 9; 1 = highest quality or darkest green.

TABLE 8

Relative Comparison of Spring Greenup rates of Rugby and other bluegrass cultivars at Woodland, California(1).

| | 1975 | 1976 | 2 Year avg. |
|---|---|---|---|
| Rugby | 4.5(2) | 5.0 | 4.8 |
| Glade | 5.5 | 5.0 | 5.3 |
| Adelphi | 5.0 | 5.5 | 5.3 |
| Parade | 1.5 | 4.0 | 2.8 |
| Baron | 5.5 | 5.5 | 5.5 |
| Fylking | 5.5 | 4.5 | 5.0 |

TABLE 8-continued

Relative Comparison of Spring Greenup rates of Rugby and other bluegrass cultivars at Woodland, California(1).

| | 1975 | 1976 | 2 Year avg. |
|---|---|---|---|
| Park | 2.0 | 6.0 | 4.0 |
| Pennstar | 4.7 | 6.7 | 5.7 |
| Merion | 3.9 | 6.0 | 5.0 |

(1)Northrup King Co. Test seeded spring 1973.
(2)1 to 9; 1 = rapid green, 9 = dormant

TABLE 9

Relative comparison of spring greenup rates of Rugby and other bluegrass cultivars at Beltsville, Maryland(1).

| | 1974 | 1975 | 1976 | 3 Year Avg. |
|---|---|---|---|---|
| Rugby | 6.0(2) | 8.6 | 7.0 | 7.2 |
| Vantage | 8.6 | 9.0 | 8.3 | 8.6 |
| Merion | 7.0 | 8.6 | 8.0 | 7.9 |
| Park | 7.0 | 8.0 | 7.3 | 7.4 |
| Parade | 7.3 | 8.3 | 6.0 | 7.2 |
| Touchdown | 6.0 | 7.6 | 6.7 | 6.8 |
| Bonnieblue | 6.3 | 7.6 | 5.7 | 6.5 |
| Adelphi | 5.3 | 7.6 | 6.3 | 6.4 |
| Majestic | 6.6 | 7.0 | 5.3 | 6.3 |
| Fylking | 5.6 | 6.6 | 5.0 | 5.7 |
| Glade | 4.0 | 5.6 | 3.7 | 4.4 |
| Victa | 3.6 | 5.3 | 4.3 | 4.4 |
| Pennstar | 4.0 | 5.0 | 4.0 | 4.3 |
| Baron | 4.0 | 4.0 | 4.3 | 4.1 |
| Nugget | 1.0 | 1.3 | 1.0 | 1.1 |

(1)USDA-ARS. Test seeded fall 1972 and maintained at 2.5 inch mowing height non-irrigated, and moderate nitrogen fertility level (2 to 3 lbs. N per thousand square feet per season.)
(2)1 to 9; 9 = rapid greenup

TABLE 10

Relative comparison of spring greenup rates of Rugby and other bluegrass cultivars at Urbana, Illinois(1).

| | 1975 | 1977 | 2 Year Avg. |
|---|---|---|---|
| Rugby | 2.7(2) | 4.7 | 3.7 |
| Parade | 2.3 | 3.3 | 2.8 |
| Bonnieblue | 3.0 | 3.0 | 3.0 |
| Majestic | 2.7 | 3.3 | 3.0 |
| Park | 2.3 | 4.3 | 3.3 |
| Adelphi | 2.7 | 4.0 | 3.4 |
| Vantage | 3.0 | 4.0 | 3.5 |
| Merion | 3.0 | 4.7 | 3.9 |
| Touchdown | 3.3 | 4.7 | 4.0 |
| Glade | 3.7 | 4.7 | 4.2 |
| Pennstar | 4.0 | 4.3 | 4.2 |
| Fylking | 4.3 | 4.3 | 4.3 |
| Victa | 5.0 | 4.0 | 4.5 |
| Baron | 5.3 | 4.0 | 4.7 |
| Nugget | 7.7 | 6.3 | 7.0 |

(1)University of Illinois. Test seeded April, 1972
(2)1 to 9; 1 = rapid greenup

TABLE 11

Relative comparison of the seedhead production in a mown turf of Rugby and other bluegrass cultivars of Urbana, Illinois(1)

| | Seedhead production May, 1973 |
|---|---|
| Rugby | 3(2) |
| Adelphi | 3 |
| Bonnieblue | 1 |
| Fylking | 1 |
| Glade | 0 |
| Merion | 1 |
| Nugget | 1 |
| Parade | 3 |
| Park | 0 |

TABLE 11-continued

Relative comparison of the seedhead production in a mown turf of Rugby and other bluegrass cultivars of Urbana, Illinois(1)

| | Seedhead production May, 1973 |
|---|---|
| Pennstar | 1 |
| Sydsport | 0 |
| Vantage | 2 |
| Victa | 4 |
| Majestic | 1 |
| Touchdown | 1 |
| Baron | 4 |

(1)University of Illinois. Test seeded April, 1972. Mown at 1.5 inches.
(2)0 to 4; 0 = no seedheads, 4 = heavy seedhead production.

TABLE 12

Relative comparison of the seedhead production in a closely mown turf of Rugby and other bluegrass cultivars at Eden Prairie, Minnesota(1).

| | Seedhead production turf mown at 0.75 inch May 31, 1976 |
|---|---|
| Rugby | 6.5(2) |
| Pennstar | 1.2 |
| Fylking | 1.0 |
| Merion | 3.2 |
| Adelphi | 2.4 |
| Glade | 1.0 |
| Baron | 2.5 |
| Victa | 2.5 |
| Vantage | 1.5 |
| Parade | 4.8 |
| Sydsport | 1.0 |
| Nugget | 4.5 |
| Newport | 6.6 |
| Park | 2.4 |

(1)Northrup King Company. Test seeded fall, 1973.
(2)1 to 9; 1 = no seedheads, 9 = heavy seedhead production.

TABLE 13

Relative Comparison of Leafspot (*Drechslera Poae*) Disease of Rugby and Other Bluegrass Cultivars Grown in a Greenhouse at Eden Prairie Minnesota(1)

| | General Severity |
|---|---|
| Rugby | 3.5(2) |
| Pennstar | 3.7 |
| Newport | 5.9 |
| Park | 6.0 |
| Fylking | 6.0 |
| Baron | 6.2 |
| A-34 | 5.0 |
| Touchdown | 3.9 |
| Glade | 6.5 |
| Bonnieblue | 3.0 |
| Victa | 3.9 |
| Vantage | 6.2 |
| Majestic | 3.2 |
| Bristol | 4.0 |
| South Dakota Certified | 8.3 |
| Nugget | 5.0 |

(1)Northrup King Co. Test seeded September 2, 1977 and inoculated November 4, 1977. Data is the average of ratings from Nov. 11 and November 17, 1977.
(2)1 to 9; 1 = no disease, 9 = dead.

TABLE 14

Relative Comparison of Leafspot (*Helminthosporium ssp*) Disease in Rugby and Other Bluegrass Cultivars at Urbana, Illinois(1)

| | 1973 | 1974 | 1975 | 3 Year Avg. |
|---|---|---|---|---|
| Rugby | 2.0(2) | 2.0 | 2.0 | 2.0 |
| Adelphi | 2.3 | 2.3 | 2.0 | 2.2 |

TABLE 14-continued

Relative Comparison of Leafspot (*Helminthosporium ssp*) Disease in Rugby and Other Bluegrass Cultivars at Urbana, Illinois(1)

| | 1973 | 1974 | 1975 | 3 Year Avg. |
|---|---|---|---|---|
| Baron | 3.3 | 2.3 | 2.7 | 2.8 |
| Bonnieblue | 2.0 | 1.7 | 2.3 | 2.0 |
| Fylking | 2.0 | 2.3 | 2.3 | 2.3 |
| Merion | 1.7 | 1.3 | 2.0 | 1.7 |
| Nugget | 2.0 | 1.3 | 1.0 | 1.4 |
| Parade | 2.0 | 2.0 | 2.3 | 2.1 |
| Park | 6.0 | 6.7 | 5.3 | 6.0 |
| Pennstar | 2.0 | 1.7 | 2.0 | 1.9 |
| Vantage | 4.0 | 4.3 | 3.7 | 4.0 |
| Victa | 2.7 | 2.0 | 2.7 | 2.5 |
| Majestic | 1.0 | 1.7 | 2.0 | 1.6 |
| Touchdown | 2.0 | 2.0 | 2.3 | 2.1 |
| Glade | 3.0 | 2.3 | 2.7 | 2.7 |

(1)University of Illinois. Test seeded April, 1972. Maintained with 4.0 lbs. N/1,000 square feet/season
(2)1 to 9; 1 = no disease, 9 = severely diseased

TABLE 15

Relative comparison of Leafspot (*Helminthosporium ssp*) Disease in Rugby and Other Bluegrass Cultivars at Beltsville, Maryland(1)

| | 1975 | 1976 | 2 Year Avg. |
|---|---|---|---|
| Rugby | 7.0(2) | 7.0 | 7.0 |
| Adelphi | 8.0 | 8.0 | 8.0 |
| Touchdown | 7.3 | 8.0 | 7.7 |
| Nugget | 6.0 | 8.0 | 7.0 |
| Bonnieblue | 7.6 | 8.0 | 7.8 |
| Majestic | 8.0 | 8.0 | 8.0 |
| Pennstar | 7.3 | 7.7 | 7.5 |
| Baron | 6.6 | 7.7 | 7.2 |
| Fylking | 7.0 | 7.3 | 7.2 |
| Victa | 7.6 | 7.3 | 7.5 |
| Merion | 8.0 | 7.3 | 7.7 |
| Parade | 8.0 | 7.3 | 7.7 |
| Glade | 5.3 | 7.0 | 6.2 |
| Vantage | 7.3 | 6.3 | 6.8 |
| Park | 4.0 | 5.3 | 4.7 |

(1)USDA-ARS. Test seeded fall 1972. Maintained at a low nitrogen level and non-irrigated.
(2)1 to 9; 1 = susceptible, 9 = resistant

TABLE 16

Relative Comparison of Fusarium Blight Damage in 1976 to Rugby and Other Bluegrass Cultivars at Urbana, Illinois(1)

| | 4#N | | | 8#N | | |
|---|---|---|---|---|---|---|
| | ¾ Inch | 1½ Inch | Avg. | ¾ Inch | 1½ Inch | Avg. |
| Rugby | 2.0(2) | 1.0 | 1.5 | 4.0 | 1.3 | 2.7 |
| Adelphi | 2.7 | 2.3 | 2.5 | 4.3 | 2.7 | 3.5 |
| Baron | 1.0 | 1.0 | 1.0 | 5.0 | 2.7 | 3.9 |
| Bonnieblue | 2.0 | 2.0 | 2.0 | 4.0 | 3.0 | 3.5 |
| Glade | 1.0 | 1.0 | 1.0 | 3.7 | 1.0 | 2.4 |
| Majestic | 3.0 | 2.0 | 2.5 | 5.0 | 2.3 | 3.7 |
| Merion | 1.7 | 1.3 | 1.5 | 3.3 | 3.0 | 3.2 |
| Nugget | 2.3 | 2.0 | 2.2 | 4.3 | 3.3 | 3.8 |
| Parade | 2.0 | 1.0 | 1.5 | 3.0 | 2.7 | 2.9 |
| Pennstar | 2.0 | 1.7 | 1.9 | 4.7 | 4.7 | 4.7 |
| Touchdown | 1.7 | 1.7 | 1.7 | 2.0 | 1.0 | 1.5 |
| Vantage | 2.7 | 2.3 | 2.5 | 4.7 | 3.7 | 4.2 |
| Victa | 2.3 | 4.0 | 3.2 | 4.3 | 3.3 | 3.8 |

(1)University of Illinois. Test seeded September, 1974. Maintained at 4.0 and 8.0 lbs. nitrogen/1,000 square feet/season.
(2)1 to 9; 1 = no damage; 9 = severe damage.

TABLE 17

Relative Comparison of Fusarium Blight Damage to Rugby and Other Bluegrass Cultivars at Urbana, Illinois(1)

| | 1974 | 1975 | 1977 | 3 Season Avg. |
|---|---|---|---|---|
| Rugby | 1.0(2) | 1.3 | 1.0 | 1.1 |
| Adelphi | 1.0 | 1.0 | 1.0 | 1.0 |
| Baron | 1.0 | 1.3 | 1.0 | 1.1 |
| Bonnieblue | 2.0 | 1.3 | 2.3 | 1.9 |
| Fylking | 3.7 | 2.3 | 3.3 | 3.1 |
| Merion | 1.3 | 1.7 | 2.0 | 1.7 |
| Nugget | 1.7 | 2.7 | 3.7 | 2.7 |
| Parade | 1.0 | 1.3 | 1.7 | 1.3 |
| Park | 2.7 | 2.0 | 1.0 | 1.9 |
| Pennstar | 1.3 | 2.0 | 3.0 | 2.1 |
| Vantage | 1.3 | 1.7 | 2.0 | 1.7 |
| Victa | 1.0 | 1.0 | 1.0 | 1.0 |
| Majestic | 1.0 | 1.0 | 1.0 | 1.0 |
| Touchdown | 1.0 | 1.0 | 2.3 | 1.4 |
| Glade | 1.0 | 1.0 | 1.0 | 1.0 |

(1)University of Illinois. Test seeded April, 1972.
(2)1 to 9; 1 = no disease, 9 = severe disease.

TABLE 18

Relative Comparasion of Fusarium Blight Damage to Rugby and Other Bluegrass Cultivars at Beltsville, Maryland(1).

| | 1975 |
|---|---|
| Rugby | 8.7(2) |
| Adelphi | 8.9 |
| Merion | 6.7 |
| Fylking | 7.3 |
| Glade | 6.7 |
| Touchdown | 6.3 |
| Baron | 5.7 |
| Victa | 7.0 |
| Vantage | 9.0 |
| Bonnieblue | 8.4 |
| Park | 9.0 |
| Majestic | 8.4 |
| Parade | 9.0 |
| Pennstar | 8.0 |
| Nugget | 7.3 |

(1)USDA-ARS. Test seeded fall 1972. Maintained at high nitrogen fertility level (4 to 5 pounds N/1,000 square feet/season), irrigated as needed, and mown at 1½ inches.
(2)1 to 9; 9 = resistant, 1 = susceptible

TABLE 19

Percent *Fusarium Roseum* Incidence in Rugby and Other Bluegrass Cultivars at Costa Mesa, California(1) in 1976.

| | Not Herbicide Treated | Herbicide(2) Treated |
|---|---|---|
| Touchdown | 0.0% | 3.0% |
| Rugby | 0.7 | 2.7 |
| Parade | 1.7 | 2.7 |
| Bonnieblue | 1.7 | 1.3 |
| Majestic | 1.7 | 5.0 |
| Adelphi | 20 | 2.3 |
| Glade | 2.0 | 34.0 |
| Merion | 2.0 | 5.3 |
| Newport | 2.0 | 5.0 |
| Victa | 2.3 | 8.3 |
| Baron | 2.7 | 6.0 |
| Vantage | 3.3 | 7.7 |
| Pennstar | 4.0 | 29.3 |
| Nugget | 13.3 | 66.7 |
| Fylking | 14.0 | 53.3 |
| Park | 20.3 | 20.7 |

(1)University of California, South Coast Field Station. Test seeded September, 1975.
(2)Linuron.

TABLE 20

Comparison of Fusarium Blight Incidence in Rugby and Other Bluegrass Cultivars at New Brunswick, New Jersey(1).

| | Number of Fusarium Blight Patches 1974 |
|---|---|
| Pennstar | 16.3 |
| Rugby | 0.3 |
| Brunswick | 6.3 |
| Touchdown | 1.3 |
| Enmundi | 1.3 |
| Parade | 1.0 |
| Adelphi | 1.7 |
| Bonnieblue | 6.0 |
| Glade | 0.7 |
| Sydsport | 1.7 |
| Majestic | 6.0 |
| Galaxy | 7.7 |
| Baron | 8.7 |
| Victa | 6.0 |
| Vantage | 2.3 |
| Fylking | 17.0 |
| Nugget | 5.3 |
| Park | 12.7 |
| L.S.D. 0.05 | 5.7 |

(1)Rutgers University. Test seeded in 1972.

TABLE 21

Dollar Spot (Sclerotinia Homeocarpa) Incidence in Rugby and Other Bluegrass Cultivars at Adelphia, New Jersey(1).

| | Number of Dollar Spots | | | |
|---|---|---|---|---|
| | | August 20, 1976 | | |
| | JULY 21, 1976 | 2.5#N/M | 4.5#N/M | 1976 MEAN |
| Rugby | 2 | 18 | 2 | 7 |
| Majestic | 2 | 3 | 0 | 2 |
| Bristol | 1 | 15 | 4 | 7 |
| Adelphi | 2 | 29 | 4 | 12 |
| Victa | 7 | 105 | 32 | 48 |
| Fylking | 20 | 89 | 43 | 51 |
| Bonnieblue | 5 | 64 | 17 | 29 |
| Baron | 37 | 142 | 47 | 75 |
| Touchdown | 27 | 208 | 69 | 101 |
| Nugget | 201 | 288 | 203 | 231 |
| Merion | 22 | 76 | 32 | 43 |

(1)Rutgers University. Test seeded September, 1974.

TABLE 22

Relative Comparison of Dollar Spot (*Sclerotinia Homeocarpa*) Damage to Rugby and Other Bluegrass Cultivars at Urbana, Illinois(1)

| | 1976 |
|---|---|
| Rugby | 2.5(2) |
| Adelphi | 2.4 |
| Baron | 3.2 |
| Bonnieblue | 3.0 |
| Glade | 3.4 |
| Majestic | 3.5 |
| Merion | 3.7 |
| Nugget | 5.4 |
| Parade | 2.9 |
| Pennstar | 4.2 |
| Touchdown | 3.7 |
| Vantage | 3.9 |
| Victa | 4.2 |

(1)University of Illinois. Test seeded September, 1974. Maintained at 4 pounds Nitrogen per thousand square feet per season. Mown at ¾ inch and 1½ inch. Data is the average of both mowing heights.
(2)1 to 9; 1 = no damage, 9 = severe damage

TABLE 23

Relative Comparison of Stem Rust (*P. Graminis*) Disease in Rugby and Other Bluegrass Cultivars at Adelphia, New Jersey(1)

| | 1975 |
|---|---|
| Rugby | 1.0(2) |
| Majestic | 0.5 |
| Adelphi | 1.0 |
| Bristol | 1.0 |
| Victa | 1.9 |
| Fylking | 2.5 |
| Bonnieblue | 1.0 |
| Baron | 2.5 |
| Touchdown | 6.3 |
| Nugget | 2.5 |
| Merion | 7.5 |

(1)Rutgers University. Test seeded September, 1974.
(2)0 to 9; 0 = no rust, 9 = severely rusted.

TABLE 24

Relative Comparison of Stem Rust (*P. Graminis*) Disease in Rugby and Other Bluegrass Cultivars at Eden Prairie, Minnesota(4)

| | 1974 |
|---|---|
| Rugby | 4.8(2) |
| Pennstar | 3.9 |
| Fylking | 4.0 |
| Merion | 6.3 |
| Adelphi | 4.6 |
| Glade | 4.0 |
| Baron | 4.5 |
| Victa | 4.8 |
| Vantage | 6.3 |
| Parade | 4.2 |
| Nugget | 5.0 |
| Newport | 3.5 |
| Park | 3.7 |
| South Dakota Certified | 4.3 |

(1)Northrup King Co. Test seeded fall of 1973.
(2)1 to 9; 1 = no rust, 9 = severely rusted.

TABLE 25

Relative Comparison of Stem Rust (*P. Graminis*) Incidence in Rugby and Other Bluegrass Cultivars at Centreville, Maryland(1) (Eastern Shore)

| | STEM RUST OCT. 1973 | STEM RUST NOV. 1973 | 1973 MEAN |
|---|---|---|---|
| Rugby | 9.0(2) | 4.0(2) | 6.5 |
| Nugget | 6.7 | 3.7 | 5.2 |
| Merion | 4.0 | 1.7 | 2.9 |
| Fylking | 8.7 | 3.3 | 6.0 |
| Glade | 9.0 | 7.0 | 8.0 |
| Touchdown | 7.7 | 4.3 | 6.0 |
| Baron | 9.0 | 2.3 | 5.7 |
| Victa | 7.0 | 2.0 | 4.5 |
| Vantage | 3.0 | 2.0 | 2.5 |
| Park | 9.0 | 5.0 | 7.0 |
| Sydsport | 7.3 | 3.0 | 5.2 |
| Bonnieblue | 5.7 | 3.3 | 4.5 |
| Majestic | 3.0 | 4.3 | 3.7 |
| Adelphi | 7.7 | 7.0 | 7.4 |
| Parade | 8.7 | 4.0 | 6.4 |
| Pennstar | 4.3 | 1.7 | 3.0 |
| A-34 | 5.7 | 3.3 | 4.5 |
| L.S.D. 5% | 3.7 | 3.0 | 3.4 |

(1)University of Maryland. Test seeded 1972.
(2)0 to 9; 9 = resistant, 0 = susceptible.

TABLE 26

Relative Comparison of Stripe Rust (*P. Striiformis*) Disease in Rugby and Other Bluegrass Cultivars at Woodland, California(1) 1974.

| | 1974 |
|---|---|
| Rugby | 2.3(2) |
| Glade | 1.0 |
| Adelphi | 1.0 |
| Parade | 2.3 |
| Baron | 3.0 |
| Fylking | 5.0 |
| Park | 2.3 |
| Pennstar | 3.7 |
| Merion | 5.0 |

(1)Northrup King Co. Test seeded spring 1973.
(2)1 to 9; 1 = no rust, 9 = severely rusted.

TABLE 27

Relative Comparison of Powdery Mildew (*Erysiphe Graminis*) Incidence in Rugby and Other Bluegrass Cultivars at Roseau, Minnesota(1).

| | June, 1976 Powdery Mildew Incidence |
|---|---|
| Rugby | 2.1(2) |
| Adelphi | 2.8 |
| Baron | 3.0 |
| Bonnieblue | 1.8 |
| Enmundi | 2.5 |
| Fylking | 3.0 |
| Glade | 2.2 |
| Majestic | 2.8 |
| Merion | 3.4 |
| Newport | 3.5 |
| Nugget | 1.0 |
| Parade | 3.3 |
| Park | 3.1 |
| Pennstar | 2.9 |
| Sydsport | 1.4 |
| Touchdown | 1.0 |
| Victa | 2.5 |
| Vantage | 3.5 |

(1)University of Minnesota. Test seeded 1975.
(2)1 to 5; 1 = resistant, 5 = susceptible.

TABLE 28

Comparison of Stripe Smut Incidence in Rugby and Other Bluegrass Cultivars at Urbana, Illinois(1)

| | Stripe Smut Incidence | |
|---|---|---|
| | 1976 | 1977 |
| Rugby | 1.3(2) | 25.0(3) |
| Adelphi | 1.7 | 0.0 |
| Baron | 2.7 | 2.3 |
| Bonnieblue | 1.3 | 0.0 |
| Fylking | 1.3 | 0.3 |
| Glade | 1.3 | 0.0 |
| Majestic | 1.3 | 0.0 |
| Merion | 1.0 | 76.6 |
| Nugget | 1.0 | 0.0 |
| Parade | 1.3 | 2.0 |
| Park | 1.7 | 20.3 |
| Pennstar | 2.0 | 13.3 |
| Touchdown | 1.7 | 0.0 |
| Vantage | 1.3 | 0.0 |
| Victa | 4.3 | 0.0 |
| Windsor | 1.0 | 90.0 |

(1)University of Illinois. Test seeded April, 1972.
(2) 1 to 9; 1 = no disease, 9 = severely diseased.
(3)Estimated percent infected tillers within two, 1 square foot squares per plot.

TABLE 29

Comparison of Stripe Smut Incidence in Rugby and Other Bluegrass Cultivars at Fairland, Maryland(1)

| | Stripe Smut MAY, 1975 |
|---|---|
| Rugby | 30(2) |
| Nugget | 13 |
| Merion | 62 |
| Fylking | 18 |
| Glade | 0 |
| Touchdown | 3 |
| Baron | 27 |
| Victa | 5 |
| Park | 0 |
| Vantage | 3 |
| Bonnieblue | 5 |
| Majestic | 3 |
| Adelphi | 3 |
| Parade | 28 |
| Pennstar | 3 |

TABLE 29-continued

Comparison of Stripe Smut Incidence in Rugby and Other Bluegrass Cultivars at Fairland, Maryland(1)

| | Stripe Smut MAY, 1975 |
|---|---|
| A-34 | 20 |

(1)University of Maryland. Test seeded 1972.
(2)Percent of plot area infected.

I claim:

1. A new and distinct cultivar of Kentucky bluegrass plant, substantially as illustrated and described herein, which is characterized by producing turf of high quality even when grown under low to moderate nitrogen fertility levels and restricted moisture, a medium dark green color, a medium leaf texture, high tiller density, rapid greening in the spring, good fall color retention, excellent low mowing tolerance, a vigorous and spreading growth habit, rapid seed germination and vigorous establishment, sustained turf quality through entire season, high resistance to common turf grass diseases, and a sustained high seed yield when managed for seed production.

* * * * *

UNITED STATES PATENT AND TRADEMARK OFFICE

CERTIFICATE OF CORRECTION

PATENT NO. : Plant 4,465

DATED : Howard E. Kaerwer

INVENTOR(S) : October 23, 1979

It is certified that error appears in the above—identified patent and that said Letters Patent is hereby corrected as shown below:

On the title page, item /73/ should read:
--Assignee: Northrup King Co.--.

Column 1, line 36, "close" should read --clone--.

Column 1, lines 11, 14, 29, 36 & 40-41; Column 2, lines 2-3 & 11
Column 3, line 31, "U.S. Plant Patent No. 4,183" should read
--Plant No. 4,183--.

Column 3, lines 33, 40 & 59: Column 4, lines 1, 18, 39 & 46,
"U.S. Plant Patent No. 4,183" should read --No. 4,183--

Signed and Sealed this

*Twenty-sixth* Day of *February 1980*

[SEAL]

*Attest:*

SIDNEY A. DIAMOND

*Attesting Officer*

*Commissioner of Patents and Trademarks*